US010352932B2

(12) United States Patent
Atwood

(10) Patent No.: US 10,352,932 B2
(45) Date of Patent: Jul. 16, 2019

(54) METHODS AND SYSTEMS FOR ANALYZING A SAMPLE WITH A CONSTRUCT COMPRISING A FLUORESCENT MOIETY AND A MAGNETIC MOIETY

(71) Applicant: Christopher Gordon Atwood, San Diego, CA (US)

(72) Inventor: Christopher Gordon Atwood, San Diego, CA (US)

(73) Assignee: Christopher Gordon Atwood, San Diego, CA (US)

( * ) Notice: Subject to any disclaimer, the term of this patent is extended or adjusted under 35 U.S.C. 154(b) by 93 days.

(21) Appl. No.: 15/520,055

(22) PCT Filed: Oct. 16, 2015

(86) PCT No.: PCT/US2015/055930
§ 371 (c)(1),
(2) Date: Apr. 18, 2017

(87) PCT Pub. No.: WO2016/064672
PCT Pub. Date: Apr. 28, 2016

(65) Prior Publication Data
US 2017/0336403 A1 Nov. 23, 2017

Related U.S. Application Data

(60) Provisional application No. 62/066,217, filed on Oct. 20, 2014.

(51) Int. Cl.
*G01N 21/64* (2006.01)
*G01N 27/74* (2006.01)
(Continued)

(52) U.S. Cl.
CPC ......... *G01N 33/558* (2013.01); *G01N 21/648* (2013.01); *G01N 21/6428* (2013.01);
(Continued)

(58) Field of Classification Search
CPC ..... C12Q 1/6834; C12Q 1/686; B01L 3/5027; B01L 2400/0481; B01L 2300/0867;
(Continued)

(56) References Cited

U.S. PATENT DOCUMENTS 7,575,934 B2 8/2009 Atwood
7,741,120 B2 6/2010 Klimov et al.
(Continued)

OTHER PUBLICATIONS

Hong et al., "Nanoscale-controlled spacing provides DNA microarrays with the SNP discrimination efficiency in solution phase," Langmuir (2005) 21(10):4257-4261.
(Continued)

*Primary Examiner* — Lore R Jarrett
(74) *Attorney, Agent, or Firm* — Morrison & Foerster LLP

(57) ABSTRACT

In one aspect, presence and/or level of an analyte within a sample is determined by use of a construct comprising a magnetic moiety and a fluorescent moiety. In one embodiment, the construct is magnetically migrated to a transparent surface and then dragged along the surface. In one aspect, an evanescent field is applied and changes in the diffusional or rotational properties of the fluorescent moiety as it migrates in and out of the evanescent field are measured by changes in its fluorescent emission, providing a measure of the interaction between the construct and a component of the sample.

23 Claims, 10 Drawing Sheets

(51) Int. Cl.
*G01N 33/58* (2006.01)
*G01N 33/542* (2006.01)
*G01N 33/543* (2006.01)
*G01N 33/558* (2006.01)

(52) U.S. Cl.
CPC ....... *G01N 21/6445* (2013.01); *G01N 33/542* (2013.01); *G01N 33/54326* (2013.01); *G01N 33/582* (2013.01); *G01N 27/745* (2013.01); *G01N 2021/6439* (2013.01); *G01N 2021/6463* (2013.01)

(58) Field of Classification Search
CPC ....... B01L 3/502723; B01L 2400/0655; B01L 2400/0638; B01L 3/50273; B01L 2300/0887; B01L 2300/087; B01L 3/502738; B01L 2300/0816; B01L 2300/0663; B01L 2200/16; B01L 2200/10; B01L 2200/082; B01L 7/52; B01L 3/502746; B01F 13/0059; B01F 11/0071; G01N 33/558; G01N 21/6428; G01N 21/648; G01N 21/6445; G01N 33/542; G01N 33/582; G01N 33/54326; G01N 2021/6463; G01N 2021/6439; G01N 27/745; G01N 33/54333
See application file for complete search history.

(56) References Cited

U.S. PATENT DOCUMENTS

| | | |
|---|---|---|
| 8,697,029 B2 | 4/2014 | Anker et al. |
| 2004/0061066 A1 | 4/2004 | Harada et al. |
| 2009/0117670 A1* | 5/2009 | Van Der Wijk ..... G01N 27/745 436/526 |
| 2009/0148847 A1* | 6/2009 | Kokoris ............. B01F 11/0071 435/6.14 |
| 2012/0149128 A1 | 6/2012 | Manneh |
| 2013/0330739 A1 | 12/2013 | Yu |

OTHER PUBLICATIONS

International Search Report and Written Opinion for PCT/US2015/055930, dated Jan. 8, 2016, 11 pages.
International Preliminary Report on Patentability for PCT/US2015/055930, dated Apr. 25, 2017, 9 pages.
Dictionary definition, evanescent field, *Wiley Electrical and Electronics Engineering Dictionary* (1st ed. 2004).

* cited by examiner

METHODS AND SYSTEMS FOR ANALYZING A SAMPLE WITH A CONSTRUCT COMPRISING A FLUORESCENT MOIETY AND A MAGNETIC MOIETY

CROSS-REFERENCE TO RELATED APPLICATIONS

This application is a U.S. National Phase of International Patent Application No. PCT/US2015/055930, filed Oct. 16, 2015, which claims priority to U.S. Provisional Patent Application No. 62/066,217, filed Oct. 20, 2014, and the content of each application is incorporated by reference herein in its entirety for all purposes.

TECHNICAL FIELD

The present disclosure relates to compositions, devices, and methods for the detection of analytes within a sample, for example, a complex biological sample, and determining the presence (or absence), level, and/or activity of said analytes. In certain aspects, said methods use one or more constructs within a controllable magnetic field, where each construct comprises a magnetic moiety connected or linked to a fluorescent moiety.

BACKGROUND

In the following discussion, certain articles and methods are described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Methods are available for the analysis of biological media, such as blood. These can be broadly classified into optical fluorescence, optical phase, electrochemical, and magnetic techniques. For example, a representative optical fluorescence method is Enzyme Linked ImmunoSorbent Assay (ELISA). Surface Plasmon Resonance (SPR) is a commonly used optical phase method. Electrochemical methods such as Differential Pulse Voltammetry (DPV) and magnetic methods such as MAgnetic Relaxation Immuno-Assay (MARIA) can also be used.

Typically the above methods contain a sensing element that requires either regeneration or replacement. Regeneration often involves treatment with a series of reagents, precluding usage outside of a controlled laboratory environment, and requiring careful consideration of calibration issues. Furthermore, the supporting hardware can be bulky and expensive. Replacement may be better suited for a non-laboratory environment (such as residential use), but recurrent cost considerations can be prohibitive to widespread usage.

The above methods also often exhibit a vulnerability to non-specific binding that interferes with accurate measurement of analyte concentration. Complex biological samples contain a plethora of molecules that may interact, even weakly, with a receptor intended to bind with an analyte molecule of interest. This may falsely overstate the measure of analyte concentration by proxy behavior, or falsely understate the measure of analyte concentration by blocking the binding of the analyte.

Because of the above disadvantages, there is a need for new methods, compositions, and/or systems that have widespread applicability for portable, inexpensive, reliable, and adaptable analysis of complex biological samples, such as blood samples for disease diagnosis.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, disclosed herein is a method for analyzing an analyte in a sample, comprising: providing a construct comprising a magnetic moiety and a fluorescent moiety connected by a linkage such that the two moieties exhibit a degree of diffusional independence from each other, wherein the fluorescent moiety and/or the linkage is capable of binding to an analyte of interest; contacting the construct with a sample to allow the fluorescent moiety and/or the linkage to interact with the analyte of interest, if present in the sample; applying a first magnetic field to the sample to migrate the construct towards a surface, wherein the first magnetic field comprises an axial magnetic field component; applying a second magnetic field to the sample to migrate the construct along the surface, wherein the second magnetic field comprises a transverse magnetic field component; applying an evanescent field to the surface sufficient to excite fluorescence in the fluorescent moiety; and measuring fluorescence emission of the fluorescent moiety indicative of the presence, level, and/or activity of the analyte of interest in the sample.

In one embodiment, the step of applying the second magnetic field comprises alternating the intensity of the transverse magnetic field component sufficient to alternate the diffusional movement of the fluorescent moiety in and out of the evanescent field.

In any of the preceding embodiments, the measuring step can comprise measuring the magnitude and/or phase of the fluorescence emission of the fluorescent moiety and/or polarization of the fluorescence emission. In one aspect, the magnitude and/or phase of the fluorescence emission provides a measure of the presence, level, and/or activity of the analyte of interest in the sample.

In any of the preceding embodiments, the fluorescent moiety and/or the linkage can comprise one or more receptors capable of specifically binding to the analyte of interest. In one aspect, the first magnetic field comprises an axial magnetic field gradient. In another aspect, the second magnetic field comprises a transverse magnetic field gradient.

In any of the preceding embodiments, the sample can comprise a biological sample.

In any of the preceding embodiments, the linkage can be selected from the group consisting of a dendritic molecule, a dendrimer molecule, a molecular chain, a chiral molecular chain, a graphene nanotube, a graphene nanorod, a polynucleotide, a polymer chain, a polynucleotide, a polypeptide, a polyaromatic molecule, a polycyclic molecule, a polymeric carbon, a polysaccharide, a macromolecule, and combinations thereof. In any of the preceding embodiments, the linkage can comprise polyethylene glycol (PEG) and/or polyethylene oxide (PEO). In one aspect, the linkage allows the magnetic moiety and the fluorescent moiety to exhibit a degree of diffusional independence from each other. In some embodiments, the linkage is between about 10 nm and about 50 nm, about 50 nm and about 100 nm, about 100 nm and about 500 nm, about 500 nm and about 1,000 nm, about 1,000 nm and about 5,000 nm, about 5,000 nm and about 10,000 nm, or about 10,000 nm and about 50,000 nm in length. In other embodiments, the linkage is between about 50 nm and about 200 nm in length. In yet other embodiments, the linkage is between about 1 nm and about 5 nm, about 5 nm and about 10 nm, about 50,000 nm and about 100,000 nm, about 100,000 nm and about 500,000 nm, or about 500,000 nm and about 1,000,000 nm in length.

In any of the preceding embodiments, the method can further comprise varying the transverse magnetic field component to distinguish specific binding between the analyte of interest and the construct from non-specific binding to the construct. In another aspect, the method can further comprise varying the transverse magnetic field component to determine the force necessary to dissociate the analyte of interest from the construct. In yet another aspect, the method can further comprise varying the transverse magnetic field component to determine the hydrodynamic behavior of the fluorescent moiety and/or the linkage under different hydrodynamic crossflow conditions.

In any of the preceding embodiments, the transverse magnetic field component of the second magnetic field can be periodically withdrawn or reduced. In one aspect, the transverse magnetic field component of the second magnetic field is periodically withdrawn or reduced while maintaining the axial magnetic field component of the first magnetic field.

In any of the preceding embodiments, the fluorescent moiety and/or the linkage can comprise asymmetric components such that hydrodynamic crossflow induces single-direction rotation of the fluorescent moiety.

In any of the preceding embodiments, the surface can allow the fluorescence emission to pass. In any of the preceding embodiments, the surface can be transparent.

In a further aspect, disclosed herein is a method for analyzing an analyte in a sample, comprising: providing a construct comprising a magnetic moiety and a fluorescent moiety connected by a linkage such that the two moieties exhibit a degree of diffusional independence from each other, wherein the fluorescent moiety and/or the linkage is capable of binding to an analyte of interest, and wherein the fluorescent moiety and/or the linkage comprises asymmetric components such that hydrodynamic crossflow induces single-direction rotation of the fluorescent moiety; contacting the construct with a sample to allow the fluorescent moiety and/or the linkage to interact with the analyte of interest, if present in the sample; applying a first magnetic field to the sample to migrate the construct towards a surface, wherein the first magnetic field comprises an axial magnetic field component; applying a second magnetic field to the sample to migrate the construct along the surface, wherein the second magnetic field comprises a transverse magnetic field component, wherein the transverse migration of the construct induces single-direction rotation of the fluorescent moiety; applying an evanescent field to the surface sufficient to excite fluorescence in the fluorescent moiety; and measuring cycling of the fluorescence emission of the fluorescent moiety, where the frequency of the cycling indicates the presence, level, and/or activity of the analyte of interest in the sample.

In one embodiment, the measuring step comprises measuring the magnitude and/or phase of the fluorescence emission of the fluorescent moiety and/or polarization of the fluorescence emission.

In any of the preceding embodiments, the fluorescent moiety and/or the linkage can comprise one or more receptors capable of specifically binding to the analyte of interest. In one aspect, the first magnetic field comprises an axial magnetic field gradient. In another aspect, the second magnetic field comprises a transverse magnetic field gradient.

In any of the preceding embodiments, the sample can comprise a biological sample.

In any of the preceding embodiments, the linkage can be selected from the group consisting of a dendritic molecule, a dendrimer molecule, a molecular chain, a chiral molecular chain, a graphene nanotube, a graphene nanorod, a polynucleic acid, a polymer chain, a polynucleotide, a polypeptide, a polyaromatic molecule, a polycyclic molecule, a polymeric carbon, a polysaccharide, a macromolecule, and combinations thereof. In any of the preceding embodiments, the linkage can comprise polyethylene glycol (PEG) and/or polyethylene oxide (PEO). In one aspect, the linkage allows the magnetic moiety and the fluorescent moiety to exhibit a degree of diffusional independence from each other. In some embodiments, the linkage is between about 10 nm and about 50 nm, about 50 nm and about 100 nm, about 100 nm and about 500 nm, about 500 nm and about 1,000 nm, about 1,000 nm and about 5,000 nm, about 5,000 nm and about 10,000 nm, or about 10,000 nm and about 50,000 nm in length. In other embodiments, the linkage is between about 50 nm and about 200 nm in length. In yet other embodiments, the linkage is between about 1 nm and about 5 nm, about 5 nm and about 10 nm, about 50,000 nm and about 100,000 nm, about 100,000 nm and about 500,000 nm, or about 500,000 nm and about 1,000,000 nm in length.

In any of the preceding embodiments, the method can further comprise varying the transverse magnetic field component to distinguish specific binding between the analyte of interest and the construct from non-specific binding to the construct. In another aspect, the method can further comprise varying the transverse magnetic field component to determine the force necessary to dissociate the analyte of interest from the construct. In yet another aspect, the method can further comprise varying the transverse magnetic field component to determine the hydrodynamic behavior of the fluorescent moiety and/or the linkage under different hydrodynamic crossflow conditions.

In any of the preceding embodiments, the transverse magnetic field component of the second magnetic field can be maintained. In another aspect, the transverse magnetic field component of the second magnetic field is maintained while maintaining the axial magnetic field component of the first magnetic field.

In any of the preceding embodiments, the evanescent field can be polarized. In any of the preceding embodiments, the surface can allow the fluorescence emission to pass. In any of the preceding embodiments, the surface can be transparent.

In still another aspect, a method for analyzing an analyte in a sample is provided, the method comprising: providing a construct comprising a magnetic moiety and a fluorescent moiety connected by a linkage such that the two moieties exhibit a degree of diffusional independence from each other, wherein the fluorescent moiety and/or the linkage is capable of binding to an analyte of interest; contacting the construct with a sample to allow the fluorescent moiety and/or the linkage to interact with the analyte of interest, if present in the sample; applying a first magnetic field to the sample to migrate the construct towards a surface, wherein the first magnetic field comprises an axial magnetic field component; applying a second magnetic field to the sample to migrate the construct along the surface, wherein the second magnetic field comprises a transverse magnetic field component; applying a polarized evanescent field to the surface sufficient to excite fluorescence in the fluorescent moiety; and measuring the fluorescence polarization angle of the fluorescent moiety indicative of the presence, level, and/or activity of the analyte of interest in the sample.

In one embodiment, the measuring step further comprises measuring the magnitude and/or phase of the fluorescence emission of the fluorescent moiety and/or polarization of the fluorescence emission.

In any of the preceding embodiments, the fluorescent moiety and/or the linkage can comprise one or more receptors capable of specifically binding to the analyte of interest. In one aspect, the first magnetic field comprises an axial magnetic field gradient. In another aspect, the second magnetic field comprises a transverse magnetic field gradient.

In any of the preceding embodiments, the sample can comprise a biological sample.

In any of the preceding embodiments, the linkage can be selected from the group consisting of a dendritic molecule, a dendrimer molecule, a molecular chain, a chiral molecular chain, a graphene nanotube, a graphene nanorod, a nucleic acid such as a polynucleotide, a polymer chain, a protein such as a polypeptide, a polyaromatic molecule, a polycyclic molecule, a polymeric carbon, a polysaccharide, a macromolecule, and combinations thereof. In any of the preceding embodiments, the linkage can comprise polyethylene glycol (PEG) and/or polyethylene oxide (PEO). In one aspect, the linkage allows the magnetic moiety and the fluorescent moiety to exhibit a degree of diffusional independence from each other. In some embodiments, the linkage is between about 10 nm and about 50 nm, about 50 nm and about 100 nm, about 100 nm and about 500 nm, about 500 nm and about 1,000 nm, about 1,000 nm and about 5,000 nm, about 5,000 nm and about 10,000 nm, or about 10,000 nm and about 50,000 nm in length. In other embodiments, the linkage is between about 50 nm and about 200 nm in length. In yet other embodiments, the linkage is between about 1 nm and about 5 nm, about 5 nm and about 10 nm, about 50,000 nm and about 100,000 nm, about 100,000 nm and about 500,000 nm, or about 500,000 nm and about 1,000,000 nm in length.

In any of the preceding embodiments, the method can further comprise varying the transverse magnetic field component to distinguish specific binding between the analyte of interest and the construct from non-specific binding to the construct. In another aspect, the method can further comprise varying the transverse magnetic field component to determine the force necessary to dissociate the analyte of interest from the construct. In yet another aspect, the method can further comprise varying the transverse magnetic field component to determine the hydrodynamic behavior of the fluorescent moiety and/or the linkage under different hydrodynamic crossflow conditions.

In any of the preceding embodiments, the transverse magnetic field component of the second magnetic field can be maintained. In another aspect, the transverse magnetic field component of the second magnetic field is maintained while maintaining the axial magnetic field component of the first magnetic field.

In any of the preceding embodiments, the surface can allow the fluorescence emission to pass. In any of the preceding embodiments, the surface can be transparent.

In another aspect, provided herein is a system for analyzing an analyte in a sample, comprising: a construct comprising a magnetic moiety and a fluorescent moiety connected by a linkage such that the two moieties exhibit a degree of diffusional independence from each other, wherein the fluorescent moiety and/or the linkage is capable of binding to an analyte of interest; a surface; means for applying a first magnetic field to the sample to migrate the construct towards the surface, wherein the first magnetic field comprises an axial magnetic field component; means for applying a second magnetic field to the sample to migrate the construct along the surface, wherein the second magnetic field comprises a transverse magnetic field component; means for applying an evanescent field to the surface sufficient to excite fluorescence in the fluorescent moiety; and means for measuring fluorescence emission of the fluorescent moiety indicative of the presence, level, and/or activity of the analyte of interest in the sample.

In one embodiment, the fluorescent moiety and/or the linkage comprises one or more asymmetric components such that hydrodynamic crossflow induces single-direction rotation of the fluorescent moiety, and the means for measuring fluorescence emission comprises means for measuring cycling of the fluorescence emission. In another embodiment, the means for applying the evanescent field comprises means for applying a polarized evanescent field to the surface sufficient to excite fluorescence in the fluorescent moiety, and the means for measuring fluorescence emission comprises means for measuring the fluorescence polarization angle of the fluorescent moiety.

In any of the preceding embodiments, the means for applying the second magnetic field can comprise means for alternating the intensity of the transverse magnetic field component sufficient to alternate the diffusional movement of the fluorescent moiety in and out of the evanescent field.

In any of the preceding embodiments, the means for measuring fluorescence emission can comprise means for measuring the magnitude and/or phase of the fluorescence emission of the fluorescent moiety.

In any of the preceding embodiments, the magnitude and/or phase of the fluorescence emission can provide a measure of the presence, level, and/or activity of the analyte of interest in the sample.

In any of the preceding embodiments, the fluorescent moiety and/or the linkage can comprise one or more receptors capable of specifically binding to the analyte of interest.

In any of the preceding embodiments, the first magnetic field can comprise an axial magnetic field gradient. In any of the preceding embodiments, the second magnetic field can comprise a transverse magnetic field gradient. In any of the preceding embodiments, the sample can be a biological sample.

In any of the preceding embodiments, the linkage can be selected from the group consisting of a dendritic molecule, a dendrimer molecule, a molecular chain, a chiral molecular chain, a graphene nanotube, a graphene nanorod, a polynucleic acid, a polymer chain, a polynucleotide, a polypeptide, a polyaromatic molecule, a polycyclic molecule, a polymeric carbon, a polysaccharide, a macromolecule, and combinations thereof. In any of the preceding embodiments, the linkage can comprise polyethylene glycol (PEG) and/or polyethylene oxide (PEO). In any of the preceding embodiments, the linkage can allow the magnetic moiety and the fluorescent moiety to exhibit a degree of diffusional independence from each other. In some embodiments, the linkage is between about 10 nm and about 50 nm, about 50 nm and about 100 nm, about 100 nm and about 500 nm, about 500 nm and about 1,000 nm, about 1,000 nm and about 5,000 nm, about 5,000 nm and about 10,000 nm, or about 10,000 nm and about 50,000 nm in length. In other embodiments, the linkage is between about 50 nm and about 200 nm in length. In yet other embodiments, the linkage is between about 1 nm and about 5 nm, about 5 nm and about 10 nm, about 50,000 nm and about 100,000 nm, about 100,000 nm and about 500,000 nm, or about 500,000 nm and about 1,000,000 nm in length.

In any of the preceding embodiments, the system can further comprise means for varying the transverse magnetic field component to distinguish specific binding between the analyte of interest and the construct from non-specific binding to the construct. In any of the preceding embodiments, the system can further comprise means for varying the transverse magnetic field component to determine the force necessary to dissociate the analyte of interest from the construct. In any of the preceding embodiments, the system can further comprise means for varying the transverse magnetic field component to determine the hydrodynamic behavior of the fluorescent moiety and/or the linkage under different hydrodynamic crossflow conditions.

In any of the preceding embodiments, the system can further comprise means for periodically withdrawing or reducing the transverse magnetic field component of the second magnetic field. In any of the preceding embodiments, the system can further comprise means for periodically withdrawing or reducing the transverse magnetic field component of the second magnetic field while maintaining the axial magnetic field component of the first magnetic field.

In any of the preceding embodiments, the system can further comprise means for maintaining the transverse magnetic field component of the second magnetic field. In any of the preceding embodiments, the system can further comprise means for maintaining the transverse magnetic field component of the second magnetic field while maintaining the axial magnetic field component of the first magnetic field.

In any of the preceding embodiments, the surface can allow the fluorescence emission to pass. In any of the preceding embodiments, the surface can be transparent.

BRIEF DESCRIPTIONS OF THE DRAWINGS

DETAILED DESCRIPTION

Figure 1:
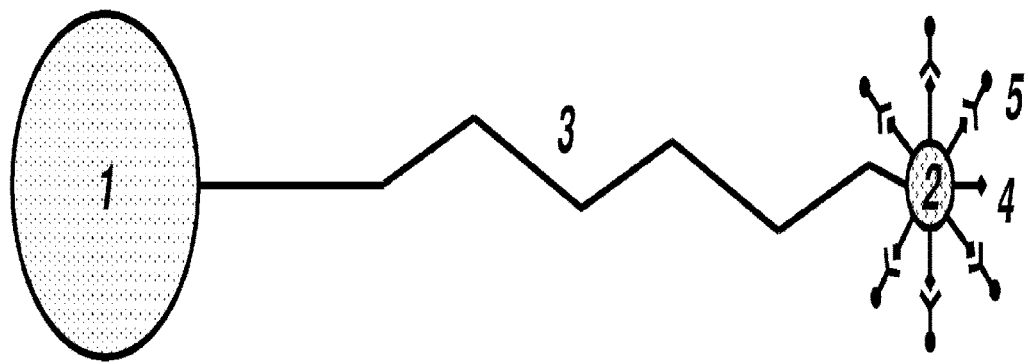
FIG. 1 is a schematic of a construct having a molecular linkage, with receptor sites on the fluorescent particle, according to one aspect of the present disclosure.
Figure 2:
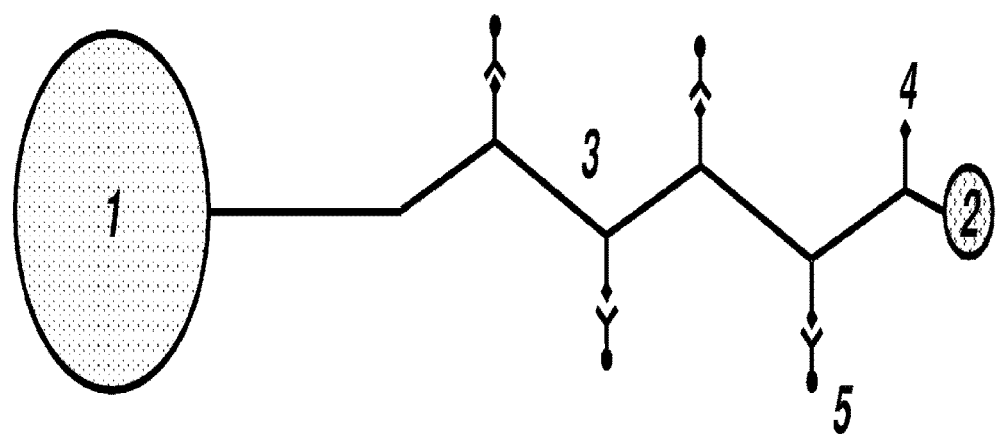
FIG. 2 is a schematic of a construct having a molecular linkage, with receptor sites on the linkage, according to one aspect of the present disclosure.

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application are incorporated by reference in their entireties for all purposes to the same extent as if each individual publication were individually incorporated by reference. If a definition set forth herein is contrary to or otherwise inconsistent with a definition set forth in the patents, patent applications, published applications or other publications that are herein incorporated by reference, the definition set forth herein prevails over the definition that is incorporated herein by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

As used herein and in the appended claims, the singular forms "a," "an," and "the" include plural referents unless the context clearly dictates otherwise. For example, "a" or "an" means "at least one" or "one or more." Thus, reference to "an analyte" refers to one or more analytes, and reference to "the method" includes reference to equivalent steps and methods disclosed herein and/or known to those skilled in the art, and so forth.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

In one aspect, disclosed herein is a technology to measure how molecules interact within a biological sample, for example, in binary, ternary, or greater interactions. In particular embodiments, compositions and methods disclosed herein are used to analyze interaction between an analyte and a binding partner, for example, within a biological sample such as blood. These methods may find widespread applicability for biomarker discovery, drug discovery, and drug evaluation. In another aspect, disclosed herein is a technology to discover the presence, absence, level, and/or activity of an analyte within a biological sample. These methods may find widespread applicability for biomarker determinations of a biological sample such as blood.

A "sample" as used herein can be any suitable material that contains an analyte of interest. In particular embodiments, a sample is a biological sample. A "biological sample" as used herein includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. In some embodiments, a biological sample includes blood, blood plasma, saliva, cerebrospinal fluid, urine, cell cultures, cell suspensions, cell lysates, any fluid of biological origin, or any fluid intended for biological usage. In some embodiments, a biological sample is a complex biological media. A biological molecule or biologically relevant molecule can be present in a biological sample, and can be detected or analyzed using a device or method of the present disclosure.

A sample as used herein can also include gelatin, agarose, polyacrylamide, polyacrylate, permeable polymers, permeable copolymers, starch, aerogel, collodion, dialysis membrane, any of the above-listed materials in a chemically modified form, and any of the above-listed materials embedded with an analyte of interest.

The term "analyte" as used herein includes molecules such as proteins, nucleic acids, lipids, carbohydrates, ions, or multicomponent complexes containing any of the above, cells, multicellular structures, subcellular components, viruses, prions, polymers, and colloids. Examples of subcellular analytes of interest include organelles, e.g., mitochondria, Golgi apparatus, endoplasmic reticulum, chloroplasts, endocytic vesicles, exocytic vesicles, vacuoles, lysosomes, etc. Exemplary nucleic acid analyte can include genomic DNA of various conformations (e.g., A-DNA, B-DNA, Z-DNA), mitochondria DNA (mtDNA), mRNA, tRNA, rRNA, hRNA, miRNA, and piRNA. The analyte may be suspended or dissolved in a sample. The analytes do not need to be biological molecules or complexes per se, but in some embodiments, the analytes are present in a biological sample, and their interaction with other components of the biological sample may be biologically relevant. For example, the interaction may be indicative of a physiological or pathological condition in the sample. In some embodiments, the analyte is a particle that is to be analyzed.

The terms "binder," "binding agent," "binding partner," "binding moiety," and "binding group" as used herein refer to any agent or any moiety or group thereof that specifically binds to an analyte molecule of interest, e.g., a biological molecule or portions or complexes thereof with other molecules.

As used herein, the term "binding" refers to an attractive interaction between two molecules which results in a stable association in which the molecules are in close proximity to each other. Molecular binding can be classified into the following types: non-covalent, reversible covalent and irreversible covalent. Molecules that can participate in molecular binding include proteins, nucleic acids, carbohydrates, lipids, and small organic molecules such as pharmaceutical compounds. For example, proteins that form stable complexes with other molecules are often referred to as receptors while their binding partners are called ligands. Nucleic acids can also form stable complex with themselves or others, for example, DNA-protein complex, DNA-DNA complex, DNA-RNA complex.

As used herein, the term "specific binding" refers to the specificity of a binder, e.g., an antibody, such that it preferentially binds to a target, such as a polypeptide antigen. When referring to a binding partner, e.g., protein, nucleic acid, antibody or other affinity capture agent, etc., "specific binding" can include a binding reaction of two or more binding partners with high affinity and/or complementarity to ensure selective hybridization under designated assay conditions. Typically, specific binding will be at least three times the standard deviation of the background signal. Thus, under designated conditions the binding partner binds to its particular target molecule and does not bind in a significant amount to other molecules present in the sample. Recognition by a binder or an antibody of a particular target in the presence of other potential interfering substances is one characteristic of such binding. Preferably, binders, antibodies or antibody fragments that are specific for or bind specifically to a target bind to the target with higher affinity than binding to other non-target substances. Also preferably, binders, antibodies or antibody fragments that are specific for or bind specifically to a target avoid binding to a significant percentage of non-target substances, e.g., non-target substances present in a testing sample. In some embodiments, binders, antibodies or antibody fragments of the present disclosure avoid binding greater than about 90% of non-target substances, although higher percentages are clearly contemplated and preferred. For example, binders, antibodies or antibody fragments of the present disclosure avoid binding about 91%, about 92%, about 93%, about 94%, about 95%, about 96%, about 97%, about 98%, about 99%, and about 99% or more of non-target substances. In other embodiments, binders, antibodies or antibody fragments of the present disclosure avoid binding greater than about 10%, 20%, 30%, 40%, 50%, 60%, or 70%, or greater than about 75%, or greater than about 80%, or greater than about 85% of non-target substances.

The term "magnetic moiety" as used herein includes molecules, colloids, and collections of atoms that form a structure that exhibits magnetic susceptibility and/or magnetic permeability and/or magnetizability and/or a magnetic moment. In some aspects, a magnetic moiety within the construct disclosed herein is a magnetic particle.

The magnetic moiety may be covered with a shell sufficient to minimize self-agglomeration of the magnetic moieties in the presence of a magnetic field. This may be accomplished through steric hindrance or electrostatic repulsion.

The magnetic moiety may have two linkages attached to it, each with a fluorophore at the distal end. When the magnetic particle is dragged along the surface, the two fluorophores are forced to be close together, allowing Forster Resonance Energy Transfer (FRET). When the dragging is halted, the two fluorophores can migrate away from each other, reducing FRET. The rate at which the fluorescence is reduced is dependent on the diffusivity of the fluorophores, which in turn is dependent on analyte binding to the fluorophores or their linkages. Similarly, such a construct may have a ligand on one fluorophore and a receptor on the other fluorophore, or other related configurations.

The measurements described herein can be performed at a series of temperatures, so that information can be obtained about the temperature dependence of the diffusional properties and binding of the analyte.

The term "fluorescent moiety" as used herein includes molecules, proteins, colloids, quantum dots, and collections of atoms that form a structure that exhibits fluorescence. The fluorescent moiety may contain receptor sites. In some aspects, a fluorescent moiety within the construct disclosed herein is a fluorescent particle.

The term "linkage" as used herein includes dendritic molecules, dendrimer molecules, molecular chains, chiral molecular chains, graphene nanotubes, graphene nanorods, polynucleic acids, polymer chains, polynucleotides, polypeptides, polyaromatic molecules, polycyclic molecules, polymeric carbon molecules, polysaccharides, macromolecules, combinations of the aforementioned, and any molecular structure that allows the magnetic moiety and the fluorescent moiety to be connected together while exhibiting a degree of diffusional independence from each other. In some embodiments, the linkage comprises polyethylene glycol (PEG) and/or polyethylene oxide (PEO). In one aspect, the linkage may contain receptor sites. In other aspects, the linkage may be rigid, flexible, or a sequence of rigid sections with one or more flexible joints. In some embodiments, the one or more flexible joints comprise receptor sites that affect movement of the fluorescent moiety.

The term "degree of diffusional independence" as used herein includes a property of a construct that comprises a magnetic moiety linked to a fluorescent moiety, where if the magnetic moiety is held in place, the fluorescent moiety is able to exhibit diffusional or rotational movement in the external environment of the magnetic moiety while maintaining a physical linkage to the magnetic moiety. In some embodiments, the construct is a heterodimer of the magnetic moiety and the fluorescent moiety. In other embodiments, the construct comprises one or more magnetic moieties. In some embodiments, the construct comprises one or more fluorescent moieties.

The term "axial magnetic field gradient" as used herein describes a magnetic field gradient that is perpendicular to the transparent surface, which may be a component of a magnetic field gradient oriented at an angle to the transparent surface.

The term "transverse magnetic field gradient" as used herein describes a magnetic field gradient that is parallel to the transparent surface, which may be a component of a magnetic field gradient oriented at an angle to the transparent surface.

The surface may comprise any of a wide variety of materials, for example, polymers, plastics, resins, polysaccharides, silica or silica-based materials, carbon, metals, inorganic glasses, membranes, or any combination of the above-listed substrate materials. In certain embodiments, the surface comprises rubber, shellac, pyroxylin (known under trade names as Celluloid, Pyrolin, etc.), phenol formaldehyde resins (trade name Bakelite), casein, urea formaldehyde resins, thiourea resin, cellulose acetate, vinyl and styrol types of plastics, and any combinations thereof. The methyl ester of methacrylic acid is an example of a plastic which may have incorporated therein glass fibers or metal. In one aspect, the surface is rigid or semi-rigid. In one aspect, the surface is flexible or soft. In one aspect, the surface is transparent. The surface may be textured with a pattern that optimizes analytical measurements. For example, the transparent surface may comprise a grating pattern or a holographic pattern, where the constructs are located in the grooves and move along the grooves. The transparent surface may be textured with a pattern that optimizes addition or removal of the construct from the sample. In some embodiments, the surface comprises the interface between two immiscible liquids. In some embodiments, the surface comprises a surface with a molecular coating.

The constructs disclosed herein can be synthesized in a number of ways. For example, magnetic nanoparticles can be treated with a PAMAM (poly(amidoamine)) dendrimer, in a manner similar to the way that Nanogea, Inc. employs its Nanocone technology on a flat surface, or as described by Bong Jin Hong et al., Langmuir 2005, Vol 21, pg. 4257-4261. In some embodiments, if the dendrimer is large enough, and the magnetic particle is small enough, then the dendrimer effectively coats the entire magnetic particle, with a single outward-directed amine group. In one aspect, this single outward-directed amine group can then be bonded to a carboxyl group with a peptide linkage reaction. A well-known peptide linkage reaction uses EDC (1-ethyl-3-(3-dimethylaminopropyl)carbodiimide) to connect an amine group with a carboxyl group. In some embodiments, sulfo-NHS (N-hydroxysulfosuccinimide) is also used to increase yield. If said carboxyl group is at the end of a long chain of PEO (polyethylene oxide) or PEG (polyethylene glycol), this causes the long chain to be attached to the single outward-directed amine group, producing a magnetic particle with a single long chain attached to it. Commercially available reagents can be used, including Biotin-PEG-carboxylic acid and Biotin-PEO-carboxylic acid, having biotin at one end of a long chain, and carboxylic acid at the other end. If such reagents are used, then this produces a magnetic particle with a single long chain attached to it and a biotin at the distal end. Addition of streptavidin-coated quantum dots (or other fluorophore) causes binding of the quantum dots to the biotin, producing a magnetic particle with a single long chain attached to it and a quantum dot at the distal end.

In some embodiments, carboxyl-coated magnetic nanoparticles are suspended in water, and an immiscible liquid layer containing DCC (N,N'-dicyclohexylcarbodiimide) is applied. DCC is insoluble in water, but soluble in various low-polarity solvents that are immiscible with water. DCC reacts with any carboxyl groups that impact the liquid boundary, forming an intermediate compound. Impact may be assisted by a magnetic field gradient axial to the liquid boundary. The magnetic particle will be held in place at the liquid boundary, unable to significantly rotate or diffuse away, due to the intermediate compound having one side polar (remaining carboxyl groups attracted to the water) and the other side non-polar (cyclohexane rings of the DCC attracted to the low-polarity solvent). Limitation of the rotation or diffusion may be enhanced by inclusion of long alkane chains to the cyclohexane rings of the DCC, functioning as anchors to the low-polarity solvent. This configuration allows only a small region of the surface of the magnetic particle to react with DCC. After the reaction, the remaining DCC is washed way. Commercially available reagents are Biotin-PEG-amine and Biotin-PEO-amine, having biotin at one end of a long chain, and amine at the other end. The water layer is treated with Biotin-PEG-amine or Biotin-PEO-amine, and the amine group reacts with the DCC group of the intermediate compound to produce a magnetic particle with a single long chain attached to it and a biotin at the distal end. Addition of streptavidin-coated quantum dots (or other fluorophore) causes binding of the quantum dots to the biotin, producing a magnetic particle with a single long chain attached to it and a quantum dot at the distal end.

In some embodiments, the EDC or DCC reagents may be chemically bonded to a surface in such a manner that its ability to form peptide bonds is maintained. Treatment of such a surface with carboxyl-coated magnetic nanoparticles will cause adherence to the surface by the formation of an intermediate compound. Next, remaining carboxyl groups can be protected or derivatized, and finally Biotin-PEG-amine or Biotin-PEO-amine is added to form peptide bonds and release the nanoparticles from the surface, to produce a magnetic particle with a single long chain attached to it and a biotin at the distal end. Addition of streptavidin-coated quantum dots (or other fluorophore) causes binding of the quantum dots to the biotin, producing a magnetic particle with a single long chain attached to it and a quantum dot at the distal end.

In the above synthesis examples, there are numerous variations that are possible, such as swapping the roles of amine and carboxyl, swapping the roles of magnetic particle and quantum dot, and replacing the long chain with another long molecule such as polynucleotide. Linkage chemistry is generally known in the art, and any suitable linkage chemistry method can be used herein. The above examples are not intended to be an exhaustive listing of the options available for linkage chemistry and construction of the constructs.

The term "hydrodynamic crossflow" as used herein describes the relative movement of solvent molecules against the construct when the construct is acted upon by a transverse magnetic field gradient, where the viscosity of the solvent molecules produces dragging forces acting on the construct and material bound to it. In some embodiments, the solvent is water.

Constructs of magnetic particles and fluorescent particles are known. These can also be referred to as nanocomposites, Janus particles, or conjugated particles. These constructs contain magnetic particles and fluorescent particles that are affixed in space relative to each other. These art structures do not exhibit diffusional independence from each other. Magnetic particles comprising one or more fluorescence detectable moieties are disclosed in U.S. Pat. No. 7,575,934 B2. Particles comprising fluorescent indicator dyes and methods of using magnetic fields and/or Brownian motion to modulate an optical property of the particle are disclosed in U.S. Pat. No. 8,697,029 B2. Multifunctional nanocomposites including a core and a shell, wherein the core and the shell are of differing materials, may have magnetic properties from a magnetic material and optical properties from an inorganic semiconductor material. These multifunctional nanocomposites are disclosed in U.S. Pat. No. 7,741,120 B2. The disclosures of all three U.S. patents are incorporated herein by reference in their entireties.

In one aspect, the devices and methods described herein are used to measure the presence and/or concentration of analytes in complex biological media. In one aspect, one or more constructs are used within a controllable magnetic field, where each construct comprises a magnetic moiety connected to a fluorescent moiety, and the linkage allows the magnetic moiety and the fluorescent moiety to exhibit a degree of diffusional independence from each other. In particular embodiments, the linkage may be rigid, flexible, or a sequence of rigid sections with flexible joints. In one aspect, the fluorescent moiety or linkage is provided with analyte receptors that can bind with analytes, and one type of emission wavelength or spectrum of fluorescent moiety is provided for each analyte to be analyzed.

In one aspect, the construct comprising a magnetic moiety and a fluorescent moiety is mixed with a biological sample containing or suspected of containing an analyte of interest. In one aspect, the analyte receptors on the construct are allowed to bind with any analytes that may be present in the complex biological media. After an incubation period for the binding to occur, an axial magnetic field gradient migrates the constructs against a transparent surface, and then a transverse magnetic field gradient drags them along the transparent surface. The resulting hydrodynamic crossflow causes the fluorescent moiety to trail the magnetic moiety, close to the transparent surface. In one aspect, binding of an analyte to a receptor on the fluorescent moiety or linkage affects the hydrodynamic behavior of the fluorescent moiety, which can be detected optically by fluorescence emission resulting from fluorescence excitation that produces an evanescent field. In one aspect, movement of the fluorescent moiety away from the transparent surface corresponds to movement out of the evanescent field with a concomitant reduction in measured fluorescence.

In some embodiments, the transparent surface is illuminated by a light source to generate an evanescent field with a decay length within the sample volume. In one aspect, a device or system disclosed herein further comprises means for changing the decay length of the evanescent field, for example, to adjust the decay length within the sample volume. In another aspect, a device or system disclosed herein further comprises a means for correlating the detected signals with the change of the decay length of the evanescent field. Several ways of changing the decay length of the evanescent field can be used. For example, the incidence angle, at which the transparent surface is being illuminated, may be varied in order to change the decay length of the evanescent field. Other ways for changing the decay length of the evanescent field include varying the wavelength of the light source.

In one embodiment, the fluorescent moiety is a quantum dot. In one aspect, the emission wavelength of the quantum dot is proportional to its physical size and hence diffusional properties. In one aspect, a narrow-band optical filter is used to limit the fluorescence measurement to a subset of fluorescent moieties having highly uniform diffusional properties. In one aspect, any analyte binding would yield a distinct deviation from the uniform diffusional properties for improved analytical performance.

In particular embodiments, the devices and methods disclosed herein find widespread applicability for portable, inexpensive, reliable, and adaptable analysis of complex biological media, such as blood samples for disease diagnosis.

In particular embodiments, the devices and methods disclosed herein require supporting hardware that is simpler and smaller than that used for conventional methods, and so presents an advantage over existing methods for portability and expense. In one aspect, the devices and methods disclosed herein are capable of being housed within a handheld unit with minimal electronics.

In particular embodiments, the sensing elements in the present disclosure are a population of constructs that are easily managed for storage, quality control, and calibration, presenting an advantage over existing methods for reliability.

In particular embodiments, a population of constructs is easily removed and adjusted, so that after one set of analyses are performed, another population of constructs can be added to the same sample for further analyses indicated by the initial population of constructs. This presents an advantage over existing methods for adaptability.

In one aspect, the transverse magnetic field gradient that drags the constructs along the transparent surface is periodically reduced (while maintaining the axial magnetic field gradient that holds the constructs against the transparent surface). This reduces the hydrodynamic trailing of the fluorescent moiety, such that it is free to diffuse away from the transparent surface. In one aspect, the rate of this diffusion is dependent on the presence of bound analyte. In one aspect, an excitation evanescent field that extends through the transparent surface produces an initial high fluorescence emission, followed by intensity decay as the fluorescent moiety diffuses out of the evanescent field. In one aspect, this intensity decay is rapid with no analyte binding to the construct, and is slow with analyte binding. In particular embodiments, multiple analytes are detected simultaneously by observing each fluorescence emission wavelength or spectrum. For example, each analyte can be recognized and specifically bound by a binding partner on a florescent moiety, and fluorescence from that florescent moiety uniquely identifies the analyte from other analytes.

In another embodiment, the transverse magnetic field gradient that drags the constructs along the transparent surface is maintained (while maintaining the axial magnetic field gradient that holds the constructs against the transparent surface). In one aspect, the linkage or fluorescent moiety contains asymmetric components such that hydrodynamic crossflow produces a single-direction rotation movement of the linkage and fluorescent moiety, such that the fluorescent moiety rotates towards and away from the transparent surface. In one aspect, the frequency and magnitude of said rotation is dependent on the presence of bound analyte. In one aspect, an excitation evanescent field that extends through the transparent surface produces a cycling fluorescence emission as the fluorescent moiety rotates in and out of the evanescent field. In one aspect, this cycling is rapid with no analyte binding, and is slow with analyte binding. In particular embodiments, multiple analytes can be detected simultaneously by observing fluorescence emission wavelength or spectrum each identifying an analyte of interest.

In one aspect, the magnetic field gradient is varied with time, and produces a concomitant variation in the frequency and magnitude of said rotation. This may provide additional data of analytical value, such as distinguishing analyte binding from non-specific binding.

In another aspect, the transverse magnetic field gradient that drags the constructs along the transparent surface is maintained (while maintaining the axial magnetic field gradient that holds the constructs against the transparent surface). In one aspect, the linkage allows rotational diffusion movement of the fluorescent moiety, such that the fluorescent moiety can rotate freely while near the transparent surface. In one aspect, the rate of this rotation is dependent on the presence of bound analyte. In one aspect, a polarized excitation evanescent field that extends through the transparent surface produces a polarized fluorescence emission that is rotated to a degree dependent on the rotational diffusion movement of the fluorescent moiety. In one aspect, the polarization is diffuse with no analyte binding, and distinct with analyte binding. In one aspect, multiple analytes can be detected simultaneously by observing each fluorescence emission wavelength or spectrum.

In certain embodiments, the methods described herein are combined with conventional semiconductor microchannel array technology, commonly referred to as "lab-on-a-chip" technology. In some embodiments, the present systems and methods are used in a suitable assay to improve assay precision, reproducibility, and/or sensitivity, particularly for the assays involving small reaction volumes. For instance, the interaction between various molecules or complexes can be assayed, e.g., interactions between nucleic acids, immunoreactions involving proteins, interactions between a protein and a nucleic acid, a ligand-receptor interaction, and small molecule and protein or nucleic acid interactions, etc.

In some embodiments, the present systems and methods are used in a multiplex assay. For example, the presence and/or amount of multiple targets, e.g., multiple nucleic acid sequences, can be assayed simultaneously by using more than one binding partner (for example, each comprised in a construct comprising a magnetic moiety and a fluorescent moiety), each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

In some embodiments, the present systems and methods are used in detecting interaction between an analyte and a plurality of constructs. In one aspect, the present methods are used in high-throughput mode, e.g., in detecting a plurality of analytes of interest, and/or interaction between or among a plurality of analytes. The interaction between a plurality of analytes and a plurality of constructs can be detected simultaneously or sequentially.

Throughout this patent specification, like reference numerals are used to denote like parts.

Referring to FIGS. 1, 2, 3, 4, 5, and 6, the present disclosure uses a population of constructs within a controlled magnetic field gradient, where each construct comprises a magnetic moiety 1 connected to a fluorescent moiety 2 by a linkage 3 that allows the magnetic moiety 1 and the fluorescent moiety 2 to exhibit a degree of diffusional independence from each other. The linkage 3 may be rigid, flexible, or a sequence of rigid sections with flexible joints. The fluorescent moiety 2 or linkage 3 is provided with analyte receptors 4 that can bind with analyte 5, one type for each emission wavelength or spectrum of fluorescent moiety 2.

Figure 7:
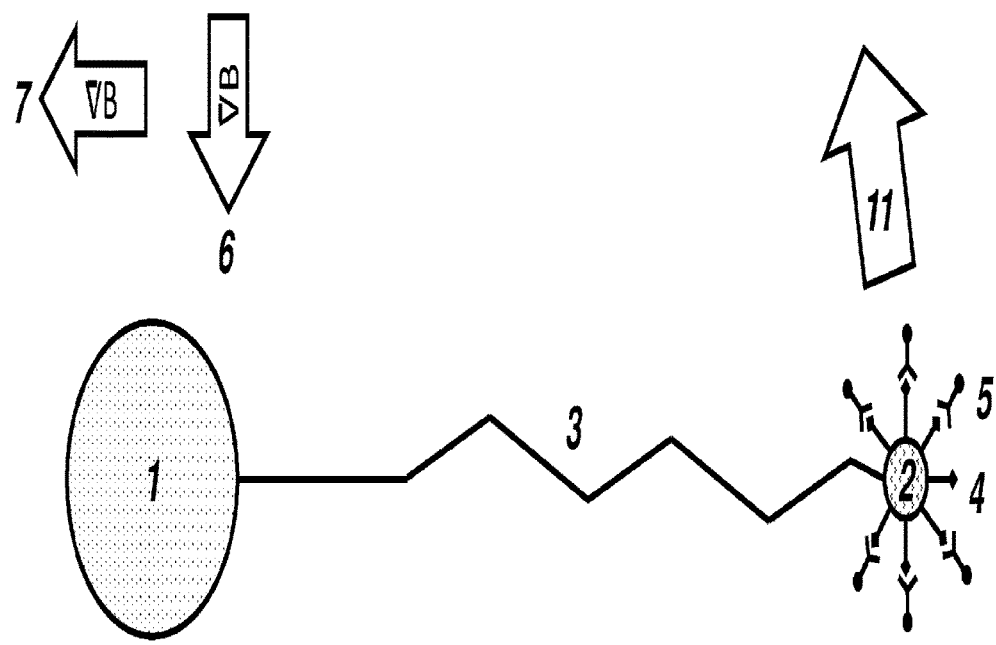
FIG. 7 is a schematic of a construct within a pair of magnetic field gradients and an evanescent field, according to one aspect of the present disclosure.
Figure 7:
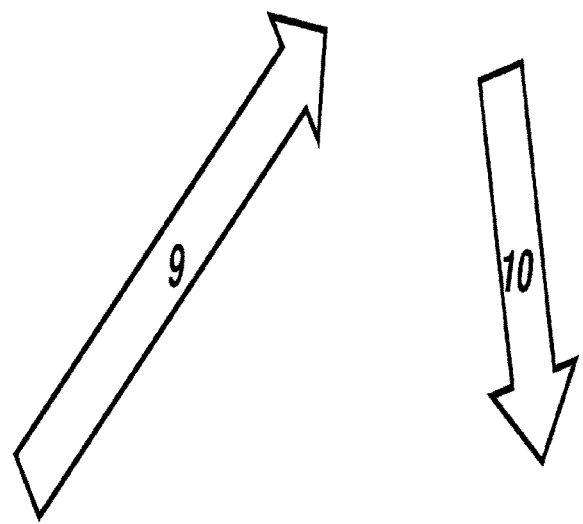

Referring to FIG. 7, the constructs are mixed with complex biological media and the analyte receptors 4 allowed to bind with any analyte 5 that may be present in the complex biological media. After an incubation period for the binding to occur, an axial magnetic field gradient 6 migrates the constructs against a transparent surface 8, and then a transverse magnetic field gradient 7 drags the constructs along the transparent surface 8. The resulting hydrodynamic crossflow causes the fluorescent moiety 2 to trail the magnetic moiety 1, close to the transparent surface 8. Binding of analyte 5 to a receptor 4 on the fluorescent moiety 2 or linkage 3 will affect the hydrodynamic behavior of the fluorescent moiety 2, which can be detected optically by fluorescence emission 10 resulting from fluorescence excitation 9 that produces an evanescent field. Movement 11 of the fluorescent moiety 2 away from the transparent surface 8 corresponds to movement out of the evanescent field with a concomitant reduction in measured fluorescence.

Referring to FIG. 7, said fluorescence excitation 9 produces said evanescent field in a manner commonly understood in the art of optics. In one example, laser light is reflected off of the boundary between the transparent surface 8 and the complex biological media such that the reflection angle is greater than the critical angle as defined by Snell's Law, yielding total internal reflection. Under these conditions, the wave vector of the laser light extends into the complex biological media for a distance of approximately one-third the wavelength of the laser light.

In one aspect, a method disclosed herein may be combined with an optical fluorescence method for detection. In one aspect, an evanescent field is generated at a transparent surface (typically a receptor-derivatized fiber optic), and changes in fluorescence are correlated to analyte presence, concentration, or activity. Fluorophores may be attached to the surface and quenched or unquenched by the binding of the analyte, or labeled to the analyte and excited upon binding of the analyte. In one aspect, the fluorophores are different from those of the construct constructs in order to distinguish fluorescence changes due to binding of an analyte to the construct and those due to binding of the analyte to the receptor-derivatized transparent surface.

In one aspect, a method disclosed herein may be combined with an optical phase method for detection. In one aspect, an evanescent field is generated at a receptor-derivatized partially-metallized transparent surface (typically a flat glass plate), and changes in refractive index near the surface are correlated to analyte presence, concentration, or activity. Refractive index is altered by the binding of analyte.

In yet another aspect, a method disclosed herein may be combined with an electrochemical method of detection. In one aspect, a receptor-derivatized metal electrode is electrically combined with a counter electrode and a reference electrode, and the potential and current are correlated to the analyte presence, concentration, or activity. Analyte binding induces a redox event either directly by a charge transfer pathway, or indirectly such as by a stripping voltammetry process.

In another aspect, a method disclosed herein may be combined with a magnetic method. In one aspect, a receptor-derivatized magnetic particle is magnetized and oriented by an externally-applied magnetic field, the field released, and the decay in the residual field from the particle is correlated to the analyte presence, concentration, or activity. Analyte binding to the surface of the magnetic particle reduces its Brownian rotational movement, slowing the decay of the residual field.

When the fluorescent moiety 2 is a quantum dot, in one aspect, then the emission wavelength of the quantum dot is proportional to its physical size and hence diffusional properties. In one aspect, a narrow-band optical filter is used to limit the fluorescence measurement to a subset of fluorescent moieties having highly uniform diffusional properties. In particular embodiments, any analyte binding would yield a distinct deviation from the uniform diffusional properties for improved analytical performance.

In particular embodiments, the fluorescent moiety 2 is a fluorescent molecule, such as fluorescein or Green Fluorescent Protein.

In particular embodiments, the linkage 3 is a polynucleic acid. In one aspect, analyte detection comprises using a complementary polynucleic acid that constrains the movement of fluorescent moiety 2.

In particular embodiments, the axial magnetic field gradient 6 and the transverse magnetic field gradient 7 may be combined into a single angled magnetic field gradient that both migrates the constructs against the transparent surface 8 and drags the constructs along the transparent surface 8.

The magnetic properties of the constructs allow various options for adding the constructs to samples, and removal after completion of the analysis. The constructs may be magnetically pulled into a sample without requiring dilution by addition of a construct suspension. Likewise, the constructs may be similarly removed from the sample once analysis is complete. Once removed, another population of constructs may be added to the sample for further investigation.

In particular embodiments, the dragging of the constructs along the transparent surface 8 produces a hydrodynamic crossflow that creates stress on material that binds to the fluorescent moiety 2 or linkage 3, due to the viscosity of the fluid environment. In one aspect, the dragging rate is increased by ramping up the intensity of the transverse magnetic field gradient 7, and the bound materials (including the analyte of interest and non-specifically bound materials) shear off at particular dragging rates, providing a determination of the binding strength of analyte 5. In one aspect, non-specifically bound materials shear off more easily than specifically bound analyte 5. In another aspect, materials that are weakly or non-specifically adsorbed are reduced by dragging, thereby reducing interference with measurement of the analyte 5.

Figure 3:
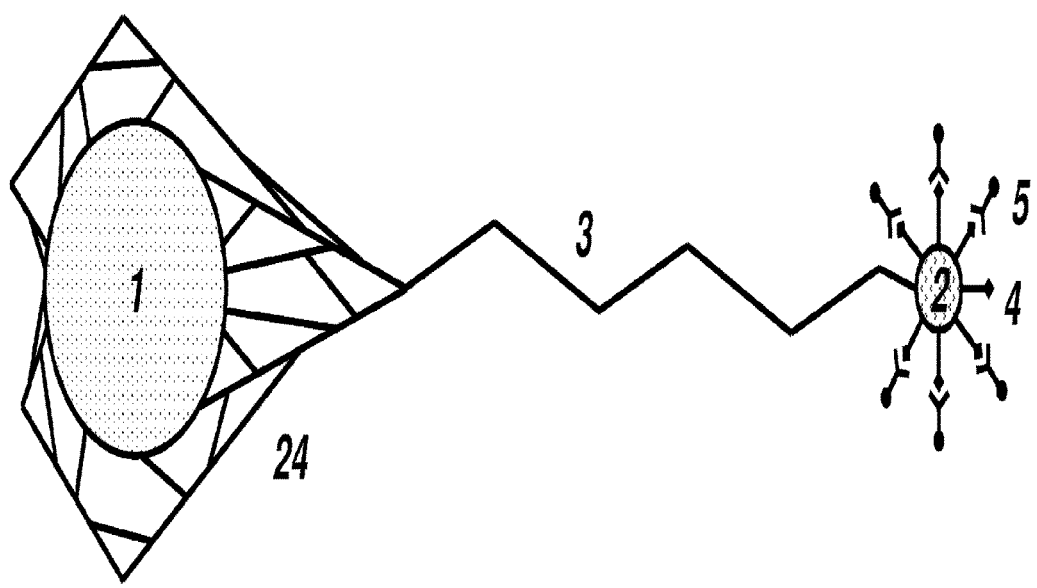
FIG. 3 is a schematic of a construct having a dendritic attachment to the magnetic particle and a single-point connection to a molecular linkage with the fluorescent particle, according to one aspect of the present disclosure.
Figure 4:
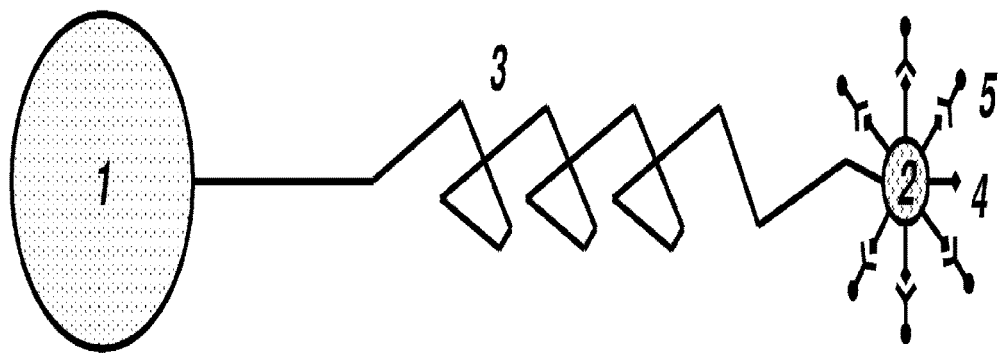
FIG. 4 is a schematic of a construct having an asymmetric linkage, according to one aspect of the present disclosure.
Figure 5:
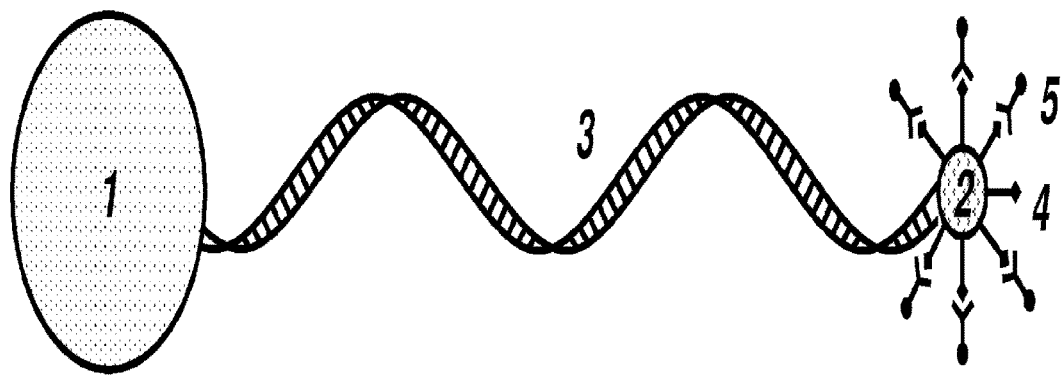
FIG. 5 is a schematic of a construct having a polynucleotide linkage, according to one aspect of the present disclosure.

Referring to FIG. 3, in one aspect, the linkage may contain a dendritic or dendrimer structure 24 that connects to the magnetic moiety 1 or fluorescent moiety 2.

Figure 6:
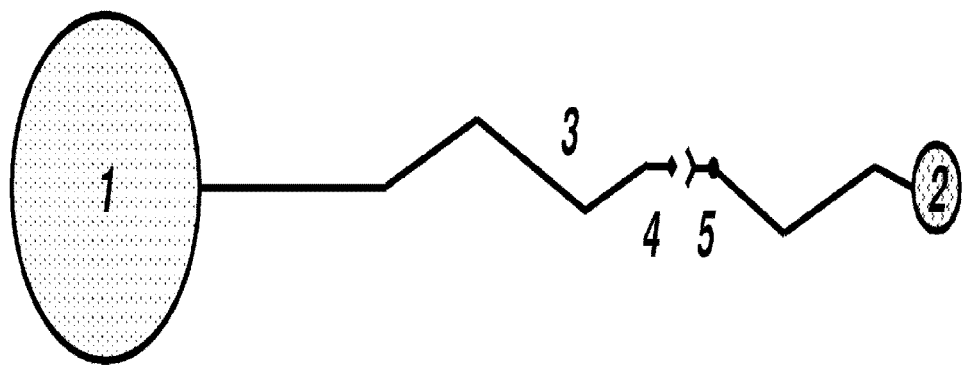
FIG. 6 is a schematic of a construct having a linkage that contains a junction composed of a bond between a receptor and an analyte, according to one aspect of the present disclosure.

Referring to FIG. 6, in one aspect, the linkage 3 may contain a junction comprising a bond between a receptor 4 and an analyte 5. In one aspect, the dragging rate is increased by ramping up the intensity of the transverse magnetic field gradient 7, the bond between receptor 4 and analyte 5 breaks at a particular dragging rate due to the hydrodynamic crossflow, providing a determination of the binding strength of the analyte 5. In one aspect, before bond breaking, the fluorescent moiety 2 is close to the transparent surface 8 and exhibits strong fluorescence; after bond breaking, the fluorescent moiety 2 is free to diffuse away from the transparent surface 8 and therefore exhibits no or reduced fluorescence.

In one aspect, the transparent surface is treated to exhibit electrostatic behavior towards the fluorescent moiety 2 or linkage 3. For example, in one embodiment, the transparent surface 8 is derivatized to have a surface charge that is the same polarity as the fluorescent moiety 2, so that movement of the fluorescent moiety 2 is directed more by electrostatic forces than by diffusion forces.

In another aspect, the magnetic moiety 1 is coated with a thick non-magnetic layer or electrostatic charge to minimize coalescence within a magnetic field.

In some embodiments, the hydrodynamic behavior of the fluorescent moiety 2 is assayed by a method disclosed herein.

In one aspect, referring to FIG. 7, the dragging of the fluorescent moiety 2 is periodically stopped in order to allow measurement of the hydrodynamic properties of the fluorescent moiety 2. This measurement is proportional to the presence of analyte 5.

Figure 8:
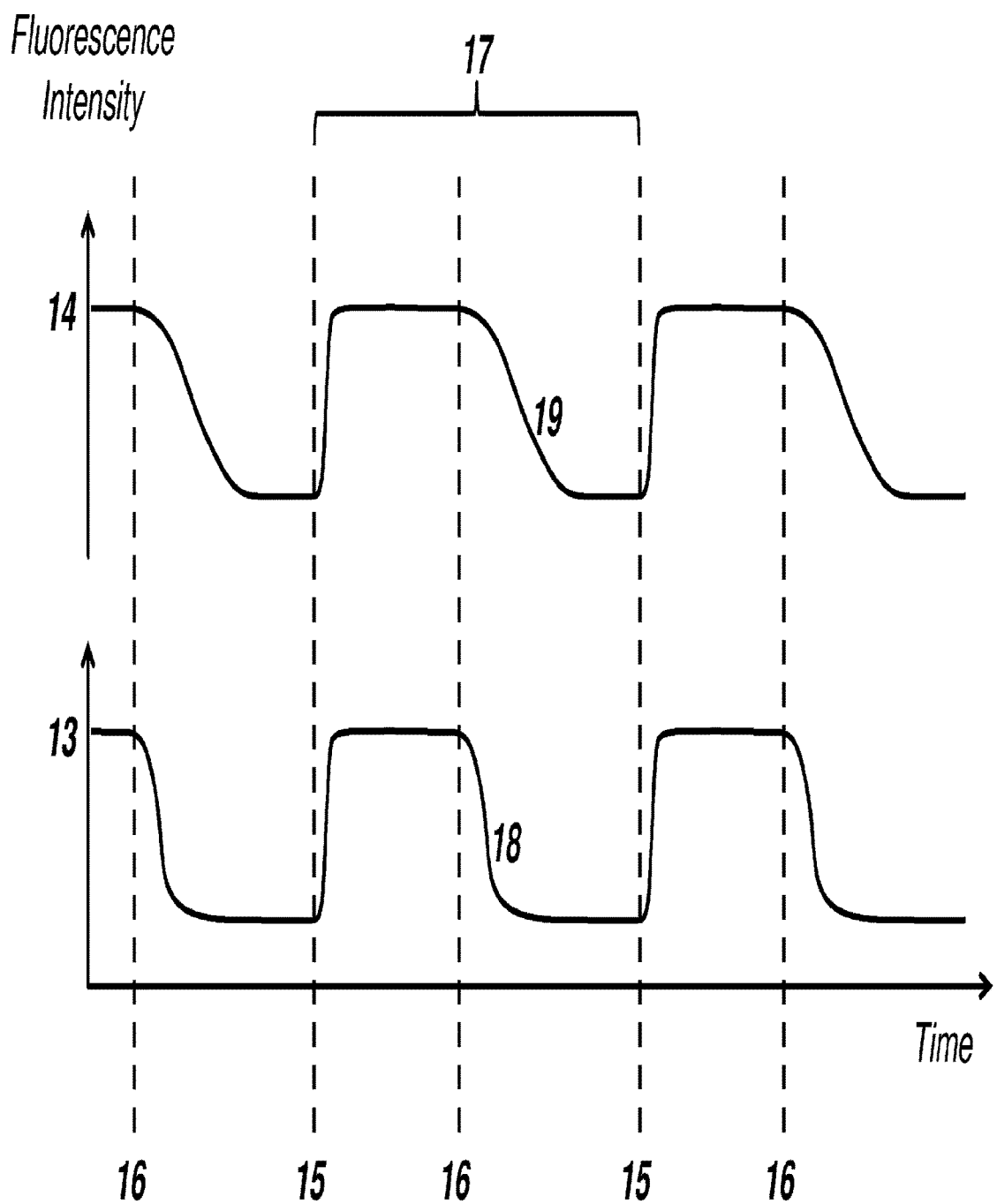
FIG. 8 illustrates fluorescence intensity as a measure of the presence (or absence), level, and/or activity of an analyte, according to one aspect of the present disclosure.

In one aspect, referring to FIG. 8, the transverse magnetic field gradient 7 that drags the constructs along the transparent surface 8 is periodically 17 reduced 16 and restored 15 (while maintaining the axial magnetic field gradient 6 that holds the constructs against the transparent surface 8). This reduces the hydrodynamic trailing of the fluorescent moiety 2, such that it is free to diffuse away from the transparent surface 8. In one embodiment, the rate of the diffusion is dependent on the presence of bound analyte 5. An excitation evanescent field that extends through the transparent surface 8 produces an initial high fluorescence emission, followed by a decay in intensity as the fluorescent moiety 2 diffuses out of the evanescent field. In one aspect, this intensity decay is rapid 18 with no analyte binding 13, and is slow 19 with analyte binding 14. Multiple analytes can be detected simultaneously by observing each fluorescence emission wavelength or spectrum.

In another embodiment, referring to FIG. 7, the dragging of the fluorescent moiety 2 causes single-direction rotation of the fluorescent moiety 2 that allows measurement of the hydrodynamic properties of the fluorescent moiety 2. In one aspect, this measurement is proportional to the amount and/or affinity of the analyte binding to the fluorescent moiety or the linkage.

Figure 9:
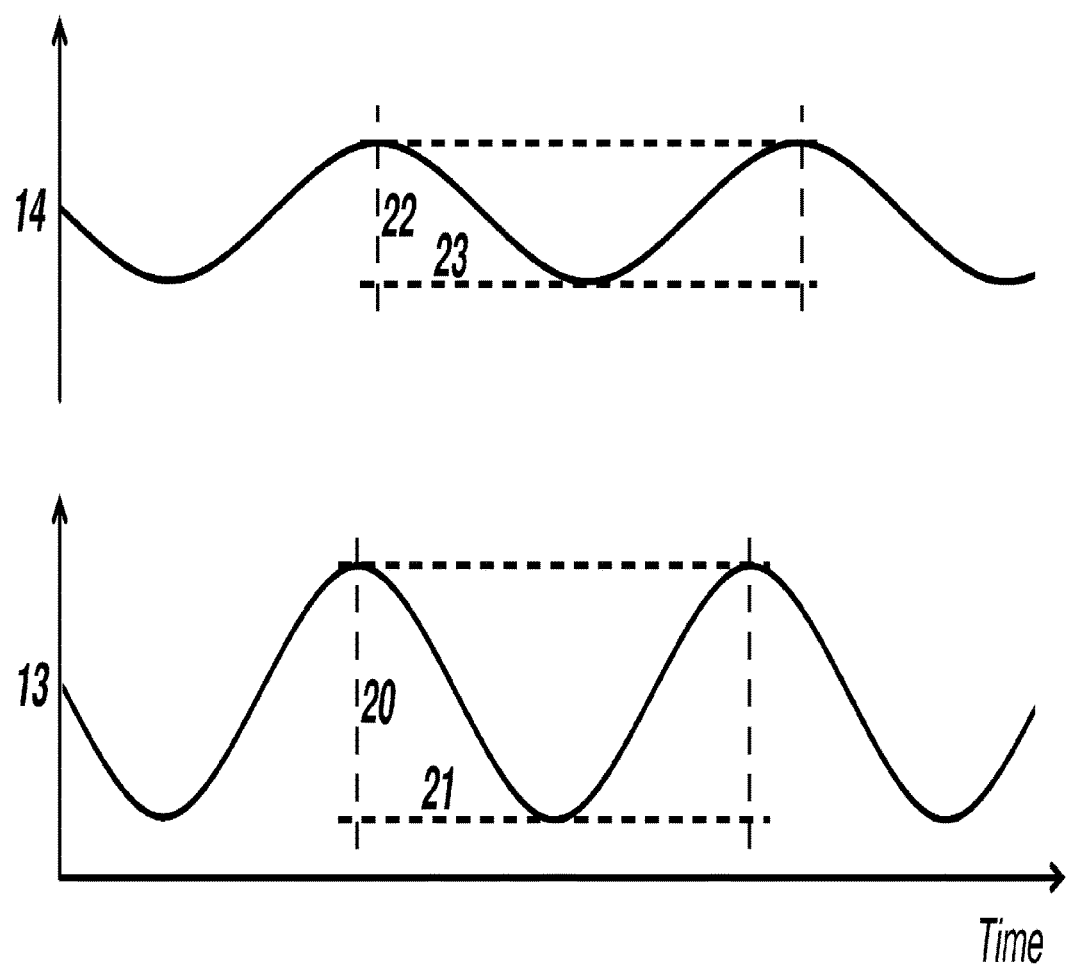
FIG. 9 illustrates cycling of fluorescence intensity as a measure of the presence (or absence), level, and/or activity of an analyte, according to one aspect of the present disclosure.

In some embodiments, referring to FIG. 9, the transverse magnetic field gradient 7 that drags the constructs along the transparent surface 8 is maintained (while maintaining the axial magnetic field gradient 6 that holds the constructs against the transparent surface 8). The linkage 3 or fluorescent moiety 2 contains asymmetric components such that hydrodynamic crossflow produces a single-direction rotation movement of the linkage 3 and fluorescent moiety 2, such that the fluorescent moiety 2 rotates towards and away from the transparent surface 8. In some embodiments, the frequency 21, 23 and magnitude 20, 22 of said rotation are dependent on the presence of bound analyte 5. In one aspect, an excitation evanescent field that extends through the transparent surface 8 produces a cycling fluorescence emission as the fluorescent moieties 2 rotate in and out of the evanescent field. In some aspects, this cycling is rapid with no analyte binding 13, and slow with analyte binding 14. Multiple analytes can be detected simultaneously by observing each fluorescence emission wavelength or spectrum.

In one aspect, the transverse magnetic field gradient 7 is varied with time, producing a concomitant variation in the frequency 21, 23 and magnitude 20, 22 of said rotation. This may provide additional data of analytical value, such as distinguishing analyte binding from non-specific binding.

In another aspect, referring to FIG. 7, the fluorescent moiety 2 exhibits random rotation that allows measurement of the hydrodynamic properties of the fluorescent moiety 2. In one aspect, this measurement is proportional to the amount and/or affinity of the analyte binding to the fluorescent moiety or the linkage.

Figure 10:
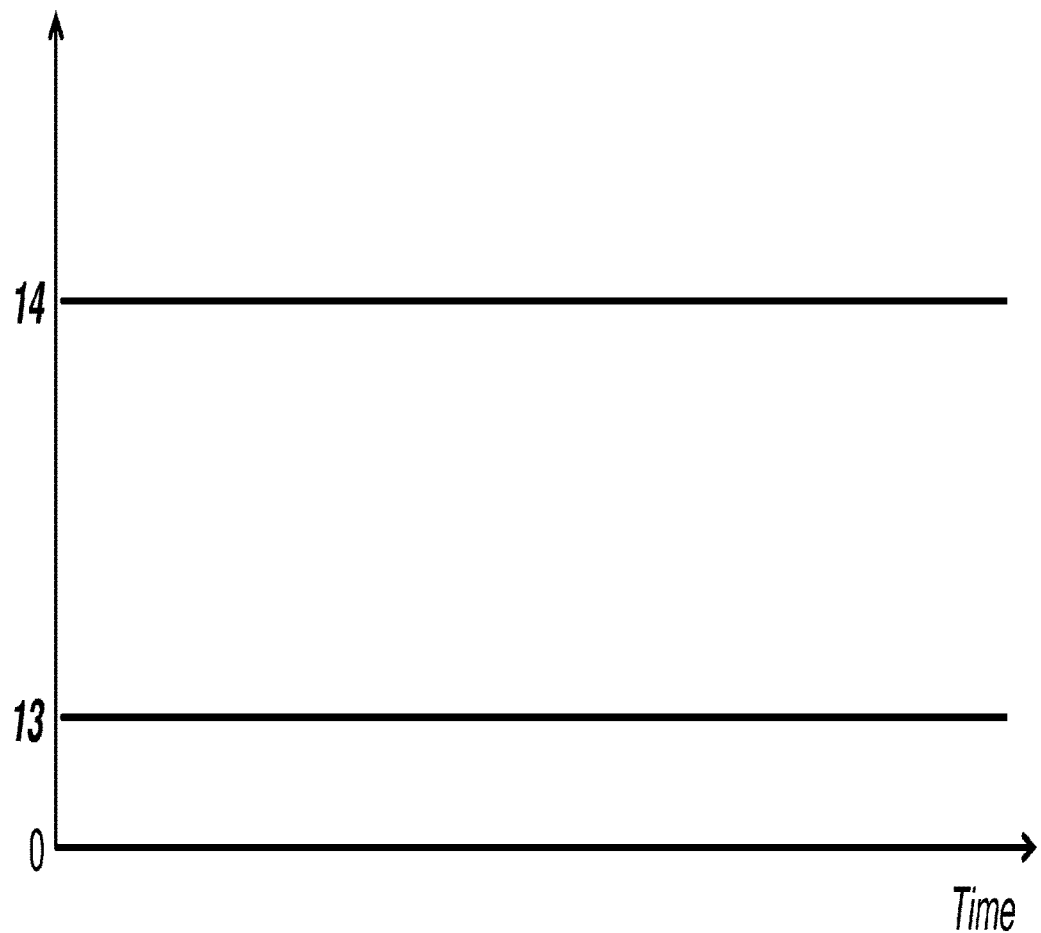
FIG. 10 illustrates fluorescence polarization angle as a measure of the presence (or absence), level, and/or activity of an analyte, according to one aspect of the present disclosure.

In some embodiments, referring to FIG. 10, the transverse magnetic field gradient 7 that drags the constructs along the transparent surface 8 is maintained (while maintaining the axial magnetic field gradient 6 that holds the constructs against the transparent surface 8). The linkage 3 allows rotational diffusion movement of the fluorescent moiety 2, such that the fluorescent moiety 2 rotates freely while near the transparent surface 8. In one aspect, the rate of this rotation is dependent on the presence of bound analyte 5. In one embodiment, a polarized excitation evanescent field that extends through the transparent surface 8 produces a polarized fluorescence emission that is rotated to a degree dependent on the rotational diffusion movement of the fluorescent moiety 2. In one aspect, this polarization angle is diffuse (closer to zero) with no analyte binding 13, and distinct with analyte binding 14.

Multiple analytes can be detected simultaneously by observing each fluorescence emission wavelength or spectrum.

In some embodiments, the methods disclosed herein are used for detection and quantitation of analytes within complex biological media. Methods in the art for performing these tasks generally suffer from a variety of deficiencies, such as requiring large and expensive support hardware, periodic cleaning or replacement of complex sensing elements, and extensive training of operating personnel. Generally, only one set of measurements can be performed on a given sample, and additional testing that is suggested by an initial set of tests would require an additional sample. There are also issues of storage, quality control, calibration, and reliability of sensing elements. These deficiencies are reduced by the methods described herein.

In one aspect, a device or method disclosed herein is used for blood analysis, for example, for monitoring drug dosage changes or variations in metabolic factors, such as glucose or cholesterol, or for detection and quantification of infectious agents such as viruses or bacteria. Blood contains a wide variety of disease markers that are currently used for disease detection and monitoring the effectiveness of drug therapies. In some aspects, a device or method disclosed herein is used for repeated or even continuous blood monitoring.

The present disclosure is further illustrated by the following exemplary embodiments:

Embodiment 1: A method for the detection of analyte presence and/or concentration within a complex biological sample, comprising: providing a construct having a magnetic particle and a fluorescent particle connected by a linkage such that the two particles exhibit a degree of diffusional independence from each other; providing analyte receptors on the fluorescent particle or linkage; immersing the construct within a sample containing an analyte; applying an axial magnetic field gradient to the sample such that the construct is forced to migrate towards a transparent surface; applying a transverse magnetic field gradient to the sample such that the construct is dragged along the transparent surface; applying an evanescent field to the transparent surface sufficient to excite fluorescence in the fluorescent particle; alternating the intensity of the transverse magnetic field gradient sufficient to alternate the diffusional movement of the fluorescent particle in and out of the evanescent field; and measuring the resultant magnitude and phase of the fluorescence emission of the fluorescent particle, wherein the magnitude and phase of the fluorescence emission provides a measure of the presence and/or concentration of an analyte.

Embodiment 2: The method of Embodiment 1, wherein said fluorescent particle contains receptor sites.

Embodiment 3: The method of Embodiment 1 or Embodiment 2, wherein said linkage is selected from the group consisting of: dendritic molecules; dendrimer molecules; molecular chains; chiral molecular chains; graphene nanotubes; graphene nanorods; polynucleic acids; polymer chains; polyethylene glycol (PEG); polyethylene oxide (PEO); any combinations of the above; and any molecular structure that allows said magnetic particle and said fluorescent particle to be connected together while exhibiting a degree of diffusional independence from each other.

Embodiment 4: The method of any one of Embodiments 1-3, wherein said linkage contains receptor sites.

Embodiment 5: The method of any one of Embodiments 1-4, wherein said linkage contains a junction comprising a bond between a receptor and an analyte.

Embodiment 6: The method of any one of Embodiments 1-5, wherein said transverse magnetic field gradient is varied, for a purpose selected from the group consisting of: distinguishing analyte from material that is non-specifically adsorbed onto said construct; determining the force necessary to sever a bond between a receptor and an analyte; and determining hydrodynamic behavior of the fluorescent particle under different hydrodynamic crossflow conditions.

Embodiment 7: A method for the detection of analyte presence and/or concentration within a complex biological sample, comprising: providing a construct having a magnetic particle and a fluorescent particle connected by a linkage such that the two particles exhibit a degree of diffusional independence from each other; structuring the linkage or fluorescent particle to have asymmetric components such that hydrodynamic crossflow will induce single-direction rotation of the fluorescent particle; providing analyte receptors on the fluorescent particle or linkage; immersing the construct within a sample containing an analyte; applying an axial magnetic field gradient to the sample such that the construct is forced to migrate towards a transparent surface; applying a transverse magnetic field gradient to the sample such that the construct is dragged along the transparent surface; applying an evanescent field to the transparent surface sufficient to excite fluorescence in the fluorescent particle; and measuring the resultant magnitude and phase of the fluorescence emission of the fluorescent particle, wherein the magnitude and phase of the fluorescence emission provides a measure of the presence and/or concentration of an analyte.

Embodiment 8: The method of Embodiment 7, wherein said fluorescent particle contains receptor sites.

Embodiment 9: The method of Embodiment 7 or Embodiment 8, wherein said linkage is selected from the group consisting of: dendritic molecules; dendrimer molecules; molecular chains; chiral molecular chains; graphene nanotubes; graphene nanorods; polynucleic acids; polymer chains; polyethylene glycol (PEG); polyethylene oxide (PEO); any combinations of the above; and any molecular structure that allows said magnetic particle and said fluorescent particle to exhibit a degree of diffusional independence from each other.

Embodiment 10: The method of any one of Embodiments 7-9, wherein said linkage contains receptor sites.

Embodiment 11: The method of any one of Embodiments 7-10, wherein said linkage contains a junction comprising a bond between a receptor and an analyte.

Embodiment 12: The method of any one of Embodiments 7-11, wherein said transverse magnetic field gradient is varied, for a purpose selected from the group consisting of: distinguishing analyte from material that is non-specifically adsorbed onto said construct; determining the force necessary to sever a bond between a receptor and an analyte; and determining hydrodynamic behavior of the fluorescent particle under different hydrodynamic crossflow conditions.

Embodiment 13: A method for the detection of analyte presence and/or concentration within a complex biological sample, comprising: providing a construct having a magnetic particle and a fluorescent particle connected by a linkage such that the two particles exhibit a degree of diffusional independence from each other; providing analyte receptors on the fluorescent particle or linkage; immersing the construct within a sample containing an analyte; applying an axial magnetic field gradient to the sample such that the construct is forced to migrate towards a transparent surface; applying a transverse magnetic field gradient to the sample such that the construct is dragged along the transparent surface; applying a polarized evanescent field to the transparent surface sufficient to excite fluorescence in the fluorescent particle; and measuring the resultant polarization of the fluorescence emission of the fluorescent particle, wherein the magnitude and phase of the fluorescence emission provides a measure of the presence and/or concentration of an analyte.

Embodiment 14: The method of Embodiment 13, wherein said fluorescent particle contains receptor sites.

Embodiment 15: The method of Embodiment 13 or Embodiment 14, wherein said linkage is selected from the group consisting of: dendritic molecules; dendrimer molecules; molecular chains; chiral molecular chains; graphene nanotubes; graphene nanorods; polynucleic acids; polymer chains; polyethylene glycol (PEG); polyethylene oxide (PEO); any combinations of the above; and any molecular structure that allows said magnetic particle and said fluorescent particle to be connected together while exhibiting a degree of diffusional independence from each other.

Embodiment 16: The method of any one of Embodiments 13-15, wherein said linkage contains receptor sites.

Embodiment 17: The method of any one of Embodiments 13-16, wherein said linkage contains a junction comprising a bond between a receptor and an analyte.

Embodiment 18: The method of any one of Embodiments 13-17, wherein said transverse magnetic field gradient is varied, for a purpose selected from the group consisting of: distinguishing analyte from material that is non-specifically adsorbed onto said construct; determining the force necessary to sever a bond between a receptor and an analyte; and determining hydrodynamic behavior of the fluorescent particle under different hydrodynamic crossflow conditions.

The invention claimed is:

1. A method for analyzing an analyte in a sample, comprising:
   contacting a sample with a construct, wherein the construct comprises a magnetic moiety and a fluorescent moiety connected by a linkage such that the two moieties exhibit a degree of diffusional independence from each other, wherein the fluorescent moiety and/or the linkage is capable of binding to an analyte of interest in the sample, thereby allowing the fluorescent moiety and/or the linkage to interact with the analyte of interest, if present in the sample;

applying a first magnetic field to the sample to migrate the construct towards a surface, wherein the first magnetic field comprises an axial magnetic field component;

applying a second magnetic field to the sample to migrate the construct along the surface, wherein the second magnetic field comprises a transverse magnetic field component;

applying an evanescent field to the surface sufficient to excite fluorescence in the fluorescent moiety; and measuring fluorescence emission of the fluorescent moiety indicative of the presence, level, and/or activity of the analyte of interest in the sample.

2. The method of claim 1, wherein the step of applying the second magnetic field comprises alternating the intensity of the transverse magnetic field component sufficient to alternate the diffusional movement of the fluorescent moiety in and out of the evanescent field.

3. The method of claim 1, wherein the measuring step comprises measuring the magnitude and/or phase of the fluorescence emission of the fluorescent moiety and/or polarization of the fluorescence emission.

4. The method of claim 3, wherein the magnitude and/or phase of the fluorescence emission provides a measure of the presence, level, and/or activity of the analyte of interest in the sample.

5. The method of claim 1, wherein the fluorescent moiety and/or the linkage comprises one or more receptors capable of specifically binding to the analyte of interest.

6. The method of claim 1, wherein the first magnetic field comprises an axial magnetic field gradient.

7. The method of claim 6, wherein the second magnetic field comprises a transverse magnetic field gradient.

8. The method of claim 1, wherein the sample is a biological sample.

9. The method of claim 1, wherein the linkage is selected from the group consisting of a dendritic molecule, a dendrimer molecule, a molecular chain, a chiral molecular chain, a graphene nanotube, a graphene nanorod, a polynucleic acid, a polymer chain, a polynucleotide, a polypeptide, a polyaromatic molecule, a polycyclic molecule, a polymeric carbon, a polysaccharide, a macromolecule, polyethylene glycol (PEG), polyethylene oxide (PEO), and combinations thereof.

10. The method of claim 1, wherein the linkage is between about 10 nm and about 50 nm, about 50 nm and about 100 nm, about 100 nm and about 500 nm, about 500 nm and about 1,000 nm, about 1,000 nm and about 5,000 nm, about 5,000 nm and about 10,000 nm, or about 10,000 nm and about 50,000 nm in length.

11. The method of claim 1, further comprising varying the transverse magnetic field component to distinguish specific binding between the analyte of interest and the construct from non-specific binding to the construct, to determine the force necessary to dissociate the analyte of interest from the construct, and/or to determine the hydrodynamic behavior of the fluorescent moiety and/or the linkage under different hydrodynamic crossflow conditions.

12. The method of claim 1, wherein the transverse magnetic field component of the second magnetic field is periodically withdrawn or reduced.

13. The method of claim 1, wherein the transverse magnetic field component of the second magnetic field is periodically withdrawn or reduced while maintaining the axial magnetic field component of the first magnetic field.

14. The method of claim 1, wherein the fluorescent moiety and/or the linkage comprises asymmetric components such that hydrodynamic crossflow induces single-direction rotation of the fluorescent moiety.

15. The method of claim 1, wherein the surface allows the fluorescence emission to pass.

16. The method of claim 1, wherein the surface is transparent.

17. The method of claim 1, wherein:
the fluorescent moiety and/or the linkage comprises asymmetric components such that hydrodynamic crossflow induces single-direction rotation of the fluorescent moiety;
in the step of applying the second magnetic field to the sample, the transverse migration of the construct induces single-direction rotation of the fluorescent moiety; and
in the measuring step, cycling of the fluorescence emission of the fluorescent moiety is measured and the frequency of the cycling indicates the presence, level, and/or activity of the analyte of interest in the sample.

18. The method of claim 1, wherein:
in the step of applying the evanescent field to the surface, the evanescent field is polarized; and
in the measuring step, a fluorescence polarization angle of the fluorescent moiety is measured, and the fluorescence polarization angle is indicative of the presence, level, and/or activity of the analyte of interest in the sample.

19. The method of claim 1, wherein the magnetic moiety is coated by a non-magnetic layer or an electrostatic charge.

20. The method of claim 1, further comprising a step of the providing the construct prior to the contacting step.

21. The method of claim 1, wherein when the magnetic moiety is held in place, the fluorescent moiety is able to exhibit diffusional or rotational movement in an external environment of the magnetic moiety while maintaining a physical linkage to the magnetic moiety.

22. A system for analyzing an analyte in a sample, comprising:
a construct comprising a magnetic moiety and a fluorescent moiety connected by a linkage such that the two moieties exhibit a degree of diffusional independence from each other, wherein the fluorescent moiety and/or the linkage is capable of binding to an analyte of interest in a sample;
a surface;
means for migrating the construct in the sample in a first magnetic field towards the surface, wherein the first magnetic field comprises an axial magnetic field component;
means for migrating the construct in the sample in a second magnetic field along the surface, wherein the second magnetic field comprises a transverse magnetic field component; and
means for applying an evanescent field to the surface sufficient to excite fluorescence in the fluorescent moiety,
wherein fluorescence emission of the fluorescent moiety is indicative of the presence, level, and/or activity of the analyte of interest in the sample.

23. A method for analyzing an analyte, comprising:
providing a construct comprising a magnetic moiety and a fluorescent moiety connected by a linkage such that the two moieties exhibit a degree of diffusional independence from each other, wherein the linkage comprises an analyte of interest bound to a binding partner, and the analyte is linked to the fluorescent moiety while the binding partner is linked to the magnetic moiety, or vice versa;

applying a first magnetic field to migrate the construct towards a surface, wherein the first magnetic field comprises an axial magnetic field component;

applying a second magnetic field to migrate the construct along the surface, wherein the second magnetic field comprises a transverse magnetic field component;

applying an evanescent field to the surface sufficient to excite fluorescence in the fluorescent moiety; and measuring fluorescence emission of the fluorescent moiety indicative of a characteristic of the analyte.

* * * * *